United States Patent [19]

Petrik et al.

[11] Patent Number: 5,120,874

[45] Date of Patent: Jun. 9, 1992

[54] PROCESS FOR THE PREPARATION OF 5-HYDROXYDIPRAFENONE AND ITS ACID ADDITION SALTS

[75] Inventors: Gerd Petrik; Klemens Schubert, both of Berlin, Fed. Rep. of Germany

[73] Assignee: Helopharm W. Petrik GmbH & Co. KG, Berlin, Fed. Rep. of Germany

[21] Appl. No.: 164,384

[22] Filed: Mar. 4, 1988

[30] Foreign Application Priority Data

Mar. 26, 1987 [EP] European Pat. Off. ........ 87104494.7

[51] Int. Cl.$^5$ .................... C07C 209/68; C07C 217/54
[52] U.S. Cl. .................... 564/349; 549/517; 564/347; 568/331
[58] Field of Search ................ 564/347, 349; 260/501.18; 549/517; 568/331

[56] References Cited

U.S. PATENT DOCUMENTS

| | | | |
|---|---|---|---|
| 3,501,769 | 5/1970 | Crowther et al. | 564/349 X |
| 3,674,840 | 7/1972 | Grandstrom et al. | 564/349 X |
| 3,929,834 | 12/1975 | Nagata | 564/349 X |
| 4,018,824 | 4/1977 | Tsukamoto et al. | 564/349 X |
| 4,283,434 | 8/1981 | DuBois et al. | 564/354 X |
| 4,336,267 | 6/1982 | Carlsson et al. | 564/349 X |
| 4,540,697 | 9/1985 | Franke et al. | 564/349 X |
| 4,571,409 | 2/1986 | Franke et al. | 564/349 X |

FOREIGN PATENT DOCUMENTS 0075207 3/1983 European Pat. Off. .
3328376 1/1985 Fed. Rep. of Germany .

OTHER PUBLICATIONS

Monecke et al., "Chemical Abstracts", vol. 68, p. 6718, Section 69421; (1968) Specifically lines 23-25 from the top.

*Primary Examiner*—Richard L. Raymond
*Attorney, Agent, or Firm*—Kenyon & Kenyon

[57] ABSTRACT

A process for the preparation of 5-hydroxydiprafenone and its acid addition salts by catalytic removal of the benzyl group of the corresponding 5-benzyloxy compound is described.

3 Claims, No Drawings

PROCESS FOR THE PREPARATION OF 5-HYDROXYDIPRAFENONE AND ITS ACID ADDITION SALTS

The invention relates to a new process for the preparation of 5-hydroxydiprafenone and its acid addition salts as well as to an essential intermediate for this process.

BACKGROUND OF THE INVENTION

German Offenlegungsschrift 33 28 376 discloses inter alia the 5-hydroxydiprafenone, i.e. the 2-[2'-hydroxy-3'-(1,1-dimethylpropylamino)-propoxy]-5-hydroxy-$\beta$-phenylpropiophenone having the following formula I:

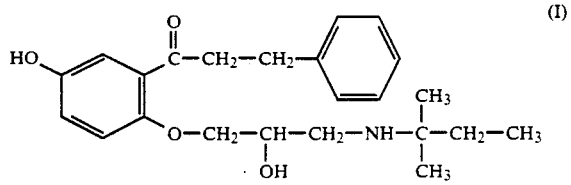

The preparation of this compound is carried out by using the correspondingly substituted acetophenone, i.e. 2,5-dihydroxy acetophenone, which after etherification of the phenolic hydroxyl group in position 2 with benzyl bromide (yield approx. 72%) which is reacted with benzaldehyde to form the corresponding $\alpha,\beta$-unsaturated ketone, i.e. 5-benzyloxy-2-hydroxy-benzalacetophenone (yield approx. 57%). This compound is reacted in almost quantitative yield with epichlorohydrine to form 2-(2',3'-epoxypropoxy)-5-benzyloxy-benzalacetophenone and then with 1,1-dimethylpropylamine to form 2-[2'-hydroxy-3'-(1,1-dimethylpropylamino)-propoxy]-5-benzyloxybenzalacetophenone. Subsequently, the 5-hydroxydiprafenone is obtained in a yield of approx. 17% of the theoretical value by catalytic hydrogenation in the presence of palladium-on-carbon (10%). The total yield of this multi-step process is about 7%. This process is not suitable for the preparation of 5-hydroxydiprafenone on an industrial scale as it is dependent on 2,5-dihydroxyacetophenone which is prepared only with a poor yield and therefore is comparatively expensive. The acylation of hydroquinone according to Friedel-Crafts results preferably in the formation of the phenolic esters.

SUMMARY OF THE INVENTION

Thus, the object underlying the invention is to provide an improved process for the preparation of 5-hydroxydiprafenone in which easily accessible starting compounds can be used and by which a considerably improved overall yield can be obtained. It is a further object of the invention to provide an essential intermediate for this process.

DETAILED DESCRIPTION OF THE INVENTION

The invention is based on the following finding: From the inexpensive and easily accessible starting compounds hydroquinone and hydrocinnamic acid ($\beta$-phenylpropionic acid) the 2,5-dihydroxy-$\beta$-phenylpropiophenone can be obtained by condensation with zinc chloride in a yield of about 86%. For the subsequent reaction, the 5-hydroxy group of this compound is provided with a protective group which can easily be removed later. The benzyl group is the preferred protective group. Then the 2-hydroxy group is etherified with epichlorohydrine under mild conditions. This reaction is preferably carried out in isopropanol as solvent and under reflux. The yield is quantitative. The product can be used without further purification in the next stage. Subsequently the resulting 2-(2',3'-epoxypropoxy)-$\beta$-phenylpropiophenone compound with the protected hydroxyl group in the 5-position is reacted under mild conditions with 1,1-dimethylpropylamine (tert-pentylamine). This reaction (opening of the epoxy ring) is preferably carried out in methanol as solvent and under reflux. The resultant 2-[2'-hydroxy-3'-(1,1-dimethylpropylamino)-propoxy]-$\beta$-phenylpropiophenone is obtained with a protected hydroxyl group in the 5-position. The protective group is easily removed from this compound in the last stage of the process. When the benzyl group is the protective group, it is removed by catalytic hydrogenation in the presence of palladium-on-carbon as catalyst. Preferably 10% palladium-on-carbon is used and the reaction is carried out at room temperature in the presence of methanol. The yield at this stage is about 73% of the theoretical value. The overall yield is at least approx. 46% of the theoretical value.

The resultant 5-hydroxydiprafenone is optionally reacted with an inorganic or organic acid to form a salt. Examples for suitable inorganic or organic acids are: hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid.

Generally the salts are obtained in a manner known per se by mixing the free base or its solutions with the corresponding acid or its solutions in an organic solvent, e.g. a lower alcohol, such as methanol, ethanol or propanol, or a lower ketone, such as acetone, methylethylketone or methylisobutylketone, or an ether, such as diethyl ether, tetrahydrofurane or dioxane. In order to improve the precipitation of crystals mixtures of the mentioned solvents may also be used.

5-Hydroxydiprafenone and its salts have antiarrhythmic properties. Thus it can be used for the treatment of cardiac arrhythmia.

The invention is illustrated by the example.

EXAMPLE a) 2,5-dihydroxy-$\beta$-phenylpropiophenone 16.5 g (120 mmole) anhydrous zinc chloride were molten with 15 g (100 mmole) hydrocinnamic acid. 11 g (100 mmole) hydroquinone were added to the resultant clear melt. This mixture was heated for 90 minutes to 160° C. After cooling, the reaction mixture was then diluted with water and washed with hydrochloric acid (10%). After removal of the aqueous phase, the remaining oil crystallized and the resultant crude product was recrystallized from water. Yield 20.8 g (86% theoretical value); m.p. 118° to 119° C.

b) 2-hydroxy-5-benzyloxy-$\beta$-phenylpropiophenone 20.8 g (86 mmole) 2,5-dihydroxy-$\beta$-phenylpropiophenone, 15.4 ml (130 mmole) benzyl bromide and 12.5 g (90 mmole) potassium carbonate were heated under reflux for 3 hours with 200 ml acetone. After distilling off the solvent, the residue was dissolved in ethylacetate and extracted three times with 150 ml each of 2N sodium hydroxide solution. Subsequently the organic phase was extracted with 150 ml 2N hydrochloric acid and then washed with water to neutrality. After that, the organic phase was separated, dried over sodium sulfate, filtered and evaporated to dryness under reduced pressure. The residue was recrystallized from ethanol/acetone (2:1).

Yield: 25.2 g (88.3% theoretical value); m.p. 65°–67° C.

c)
2-(2′,3′-epoxypropoxy)-5-benzyloxy-β-phenylpropiophenone 25.2 g (75.9 mmole) 2-hydroxy-5-benzyloxy-β-phenylpropiophenone were heated under reflux for 6 hours with 50 ml epichlorohydrine, 3.4 g sodium hydroxide and 50 ml isopropanol. Afterwards the composition was filtrated while hot and the filtrate was evaporated to dryness under reduced pressure.

The residue was used without purification for the next stage. Yield quantitative.

d)
2-[2′-hydroxy-3′-(1,1-dimethylpropylamino)-propoxy]-5-benzyloxy-β-phenylpropiophenone 20.7 g (75.9 mmole) 2-(2′,3′-epoxypropoxy)-5-benzyloxy-β-phenylpropiophenone were heated under reflux for 3 hours with 50 ml tert-pentylamine in 300 ml methanol. After evaporation under reduced pressure, the residue was heated with 200 ml methanol. After cooling, 3.2 g of a by-product were sucked off. The filtrate was evaporated to dryness under reduced pressure. The residue was used without purification in the next stage. Yield: 30.4 g (84.3% theoretical value).

e) 5-hydroxydiprafenone-hydrochloride 30.4 g (64 mmole) 2-[2′-hydroxy-3′-(1,1-dimethylpropylamino)-propoxy]-5-benzyloxy-β-phenylpropiophenone were dissolved in 250 ml methanol and hydrogenated in the presence of 1 g Pd/C (10%). After the absorption of hydrogen was completed (consumption: 1450 ml), the catalyst was filtered off and the solvent distilled off. The residue was boiled with 100 ml 1N hydrochloric acid. On cooling crystals formed which were then sucked off and recrystallized from acetone/ethanol (2:1). Yield: 19.8 g (73% theoretical value; 46.8 mmole corresponds to 46.8% theoretical value, based on hydroquinone); m.p. 165°–167° C.

What is claimed is:

1. 2-[2′-hydroxy-3′-(1,1-dimethylpropylamino)-propoxy]-5-benzyloxy-β-phenylpropiophenone.

2. A process for the preparation of 5-hydroxydiprafenone of the formula:

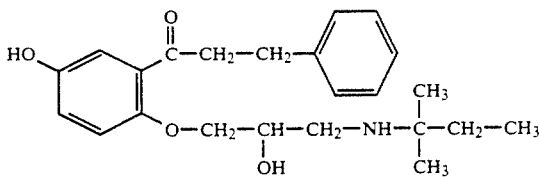

comprising the following steps:
  a) reacting hydroquinone with hydrocinnamic acid in the presence of zinc chloride;
  b) reacting the resultant 2,5-dihydroxy-B-phenylpropiophenone with benzyl bromide to form 2-hydroxy-5-benzyloxy-B-phenylpropiophenone;
  c) reacting this compound with epichlorohydrine to form 2-(2′,3′-epoxypropoxy)-5-benzyloxy-B-phenylpropiophenone;
  d) reacting this compound with 1,1-dimethylpropylamine to form 2-[2′-hydroxy-3′-(1,1-dimethylpropylamino)-propoxy]-5-benzyloxy-B-phenylpropiophenone; and
  e) hydrogenating this compound in the presence of palladium-on-carbon as catalyst to form 5-hydroxydiprafenone.

3. The process according to claim 2, further comprising the step of reacting 5-hydroxydiprafenone with an acid to form a salt.

* * * * *